US00PP28851P3

(12) United States Plant Patent
Koning

(10) Patent No.: US PP28,851 P3
(45) Date of Patent: Jan. 2, 2018

(54) ***LAVANDULA* PLANT NAMED 'ANOUK DELUXE 169'**

(50) Latin Name: *Lavandula stoechas*
Varietal Denomination: Anouk Deluxe 169

(71) Applicant: Lammert Koning, Nuis (NL)

(72) Inventor: Lammert Koning, Nuis (NL)

(73) Assignee: L. Koning Beheer B.V., Nuis (NL)

( * ) Notice: Subject to any disclaimer, the term of this patent is extended or adjusted under 35 U.S.C. 154(b) by 0 days.

(21) Appl. No.: 14/999,138

(22) Filed: Mar. 31, 2016

(65) Prior Publication Data

US 2017/0290249 P1 Oct. 5, 2017

(51) Int. Cl.
*A01H 5/02* (2006.01)

(52) U.S. Cl.
USPC ..... Plt./445

(58) Field of Classification Search
USPC ..... Plt./445
See application file for complete search history.

(56) References Cited

PUBLICATIONS

PLUTO Plant Variety database Mar. 2, 2017. p. 1.*

* cited by examiner

*Primary Examiner* — Annette Para
(74) *Attorney, Agent, or Firm* — C. A. Whealy

(57) ABSTRACT

A new and distinct cultivar of *Lavandula* plant named 'Anouk Deluxe 169', characterized by its upright plant habit; freely branching growth habit; dense and bushy appearance; strong durable plants; freely flowering habit; dark purple to dark violet blue-colored flowers with red purple to purple-colored terminal flower bracts positioned on strong and erect peduncles; strong re-flowering habit; and good garden performance.

2 Drawing Sheets

Botanical designation: *Lavandula stoechas.*
Cultivar denomination: 'ANOUK DELUXE 169'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 169'.

The new *Lavandula* plant is a product of a planned breeding program conducted by the Inventor in Nuis, The Netherlands. The objective of the breeding program was to develop new unique *Lavandula* plants with good performance and attractive plant form and flower coloration.

The new *Lavandula* plant originated from a cross-pollination made by the Inventor in May, 2011 of *Lavandula stoechas* 'Anouk', disclosed in U.S. Plant Pat. No. 16,685, as the female, or seed, parent with a proprietary selection of *Lavandula stoechas* identified as code number 1252, not patented, as the male, or pollen, parent. The new *Lavandula* plant was discovered and selected by the Inventor as a single flowering plant within the progeny of the stated cross-pollination in a controlled environment in Nuis, The Netherlands in May, 2012.

Asexual reproduction of the new *Lavandula* plant by terminal cuttings in a controlled greenhouse environment in Boskoop, The Netherlands since August, 2012 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 169' as a new and distinct *Lavandula* plant:

1. Upright plant habit.
2. Freely branching growth habit; dense and bushy appearance.
3. Strong durable plants.
4. Freely flowering habit.
5. Dark purple to dark violet blue-colored flowers with red purple to purple-colored terminal flower bracts positioned on strong and erect peduncles.
6. Strong re-flowering habit.
7. Good garden performance.

Plants of the new *Lavandula* differ primarily from plants of the female parent, 'Anouk', in the following characteristics:

1. Plants of the new *Lavandula* have a stronger re-flowering habit than plants of 'Anouk'.
2. Plants of the new *Lavandula* and 'Anouk' differ in terminal flower bract color as plants of 'Anouk' have violet-colored terminal flower bracts.

Plants of the new *Lavandula* differ primarily from plants of the male parent selection in the following characteristics:

1. Plants of the new *Lavandula* are more upright than plants of the male parent selection.
2. Plants of the new *Lavandula* have smaller terminal flower bracts than plants of the male parent selection.

Plants of the new *Lavandula* can be compared to plants of the *Lavandula stoechas* 'Sanne', disclosed in U.S. Plant Pat. No. 20,632. In side-by-side comparisons, plants of the new *Lavandula* differ primarily from plants of 'Sanne' in the following characteristics:

1. Plants of the new *Lavandula* are more upright than plants of 'Sanne'.
2. Plants of the new *Lavandula* and 'Sanne' differ in terminal flower bract color as plants of 'Sanne' have purple-colored terminal flower bracts.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* have a stronger re-flowering habit than plants of 'Toscane'.
2. Plants of the new *Lavandula* and 'Toscane' differ in terminal flower bract color as plants of 'Toscane' have light purple-colored terminal flower bracts.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical flowering plant of 'Anouk Deluxe 169' grown in a container.

The photograph on the second sheet is a close-up view of typical leaves and an inflorescence of 'Anouk Deluxe 169'.

DETAILED BOTANICAL DESCRIPTION

Plants used in the aforementioned photographs and following detailed description were grown in 3-liter containers during the winter and early spring in a glass-covered greenhouse in Boskoop, The Netherlands and under cultural practices typical of commercial *Lavandula* production. Plants were 21 months old when the photographs and description were taken. During the production of the plants, day temperatures ranged from 5° C. to 25° C. and night temperatures ranged from 5° C. to 15° C. In the following description, color references are made to The Royal Horticultural Society Colour Chart, 2015 Edition, except where general terms of ordinary dictionary significance are used.

Botanical classification: *Lavandula stoechas* 'Anouk Deluxe 169'.

Parentage:

*Female, or seed, parent.*—*Lavandula stoechas* 'Anouk', disclosed in U.S. Plant Pat. No. 16,685.

*Male, or pollen, parent.*—Proprietary selection of *Lavandula stoechas* identified as code number 1252, not patented.

Propagation:

*Type.*—Terminal vegetative cuttings.

*Time to initiate roots, summer and winter.*—About ten days at temperatures about 18° C.

*Time to produce a rooted young plant, summer.*—About 60 days at temperatures about 20° C.

*Time to produce a rooted young plant, winter.*—About 70 days at temperatures about 20° C.

*Root description.*—Fine, fibrous; initially white in color and becoming more brown with development; actual color of the roots is dependent on substrate composition, water quality, fertilizer type and formulation.

*Rooting habit.*—Freely branching; dense.

Plant description:

*Plant and growth habit.*—Herbaceous perennial; upright plant habit; freely branching habit, dense and bushy appearance; moderately vigorous growth habit; flowers arranged in verticillasters on crowded spikes with showy terminal flower bracts.

*Plant height, soil level to top of foliar plane.*—About 47.9 cm.

*Plant height, soil level to top of floral plane.*—About 48.3 cm.

*Plant width.*—About 52.8 cm.

*Lateral branch description.*—Quantity per plant: About 17 primary lateral branches developing per plant with numerous secondary branches. Length: About 24 cm. Diameter: About 2.5 mm. Internode length: About 1.4 mm. Strength: Moderately strong. Aspect: Upright to about 35° from vertical. Texture and luster: Moderately tomentose; matte. Color, developing: Close to 144B to 144C; pubescence, close to 157D. Color, developed: Close to 199A and 199B.

*Leaf description.*—Arrangement: Opposite, simple; sessile. Length: About 3.7 cm. Width: About 5.5 mm. Shape: Narrowly oblanceolate. Apex: Acute. Base: Cuneate. Margin: Entire; revolute. Texture and luster, upper and lower surfaces: Moderately tomentose; matte. Fragrance: Strongly aromatic, pungent. Venation pattern: Pinnate. Color: Developing leaves, upper surface: Close to 143A. Developing leaves, lower surface: Close to 143B to 143C. Fully expanded leaves, upper surface: Close to NN137C; venation, close to NN137C; pubescence, close to 157D. Fully expanded leaves, lower surface: Close to 138B; venation, close to 138B to 138C; pubescence, close to 157D.

Flower description:

*Flower type, arrangement and habit.*—Small single salverform flowers arranged in compact verticillasters on crowded terminal spikes; freely flowering, about 100 flowers developing per inflorescence and about 1,700 flowers developing per plant; flowers with two-lobed upper lip and three-lobed lower lip; flowers face mostly outwardly on the spike; inflorescences with showy terminal flower bracts.

*Natural flowering season.*—Long flowering period; continuous from late spring into the summer in The Netherlands; strong re-flowering habit.

*Flower longevity on the plant.*—Individual flowers last about ten days on the plant; flowers not persistent.

*Fragrance.*—None detected.

*Flower buds.*—Length: About 3 mm. Diameter: About 1 mm. Shape: Elliptic. Texture and luster: Moderately tomentose; matte. Color: Close to 143C; towards the base, close to 144C and 144D; pubescence, close to 157D.

*Inflorescence size.*—Height: About 4.8 cm. Diameter, at terminal flower bracts: About 1.8 cm. Diameter, below flower bracts: About 1.5 cm.

*Flower size*.—Diameter: About 4.5 mm. Depth (height): About 8.5 mm. Throat diameter: About 1 mm. Tube length: About 5 mm. Tube diameter: About 1 mm.

*Petals*.—Quantity and arrangement: Upper lip, two-lobed and lower lip, three-lobed. Length, upper lip: About 8 mm. Length, lower lip: About 7 mm. Width, upper lip: About 2 mm. Width, lower lip: About 1.5 mm. Shape: Roughly spatulate; lower 75% fused into a tube. Apex: Obtuse. Margin: Entire. Texture and luster, upper (inner) surface: Smooth, glabrous, velvety; matte. Texture and luster, lower (outer) surface: Smooth, glabrous, moderately velvety; slightly glossy. Color: When opening and fully opened, upper (inner) surface: Close to between 79A, N92A and 203B; with development, color becoming closer to between N92A and 203B; throat, close to N87B. When opening and fully opened, lower (outer) surface: Close to between 79A, N92A and 203B; with development, color becoming closer to between N92A and 203B; tube, close to N87D.

*Terminal flower bracts*.—Quantity and arrangement: About five positioned upright at inflorescence apex. Length: About 2.3 cm. Width: About 7 mm. Shape: Narrowly obovate to narrowly oblong. Apex: Broadly acute to obtuse. Base: Narrowly cuneate. Margin: Entire; moderately undulate. Texture and luster, upper and lower surfaces: Moderately tomentose (minute hairs); matte. Color, upper surface: Close to between 70A and N77B; midvein, close to N77C; pubescence, close to 156C and 156D. Color, lower surface: Close to between 70A and N77B; midvein, close to 184B; pubescence, close to 156C and 156D.

*Basal flower bracts*.—Quantity and arrangement: Each group of five flowers is subtended by a single basal flower bract. Length: About 6 mm. Width: About 6 mm. Shape: Broadly rhomboidal. Apex: Broadly aristate. Base: Cuneate. Margin: Entire. Texture and luster, upper and lower surfaces: Densely tomentose; matte. Color, upper and lower surfaces: Close to 145D; venation, close to 143A tinged with close to 197B; pubescence, close to NN155C.

*Sepals*.—Quantity and arrangement: Five, fused into a campanulate tube. Length: About 4 mm. Width: About 0.5 mm. Shape: Lanceolate. Apex: Acute. Margin: Entire. Texture and luster, upper (inner) and lower (outer) surfaces: Densely pubescent; matte. Color: When opening and fully opened, upper (inner) surface: Close to 144D; venation, close to 144A; pubescence, close to NN155C. When opening and fully opened, lower (outer) surface: Close to 143B; towards the apex, tinged with close to 197C; pubescence, close to NN155C.

*Peduncles*.—Length: About 5.4 cm. Diameter: About 2 mm. Aspect: Mostly upright. Strength: Strong. Texture and luster: Densely tomentose; matte. Color: Close to 147B to 147C; pubescence, close to 157D.

*Reproductive organs*.—Stamens: Quantity per flower: Four. Filament length: About 1 mm. Filament color: Close to 86A. Anther shape: Reniform. Anther length: About 0.2 mm. Anther color: Close to between N92A and 203B. Pollen amount: Moderate. Pollen color: Close to 14A. Pistils: Quantity per flower: One. Pistil length: About 4.5 mm. Stigma shape: Club-shaped. Stigma color: Close to 203A to 203B. Style length: About 4 mm. Style color: Close to 197C to 197D. Ovary color: Close to 143B to 143C.

*Seeds and fruits*.—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 169' as illustrated and described.

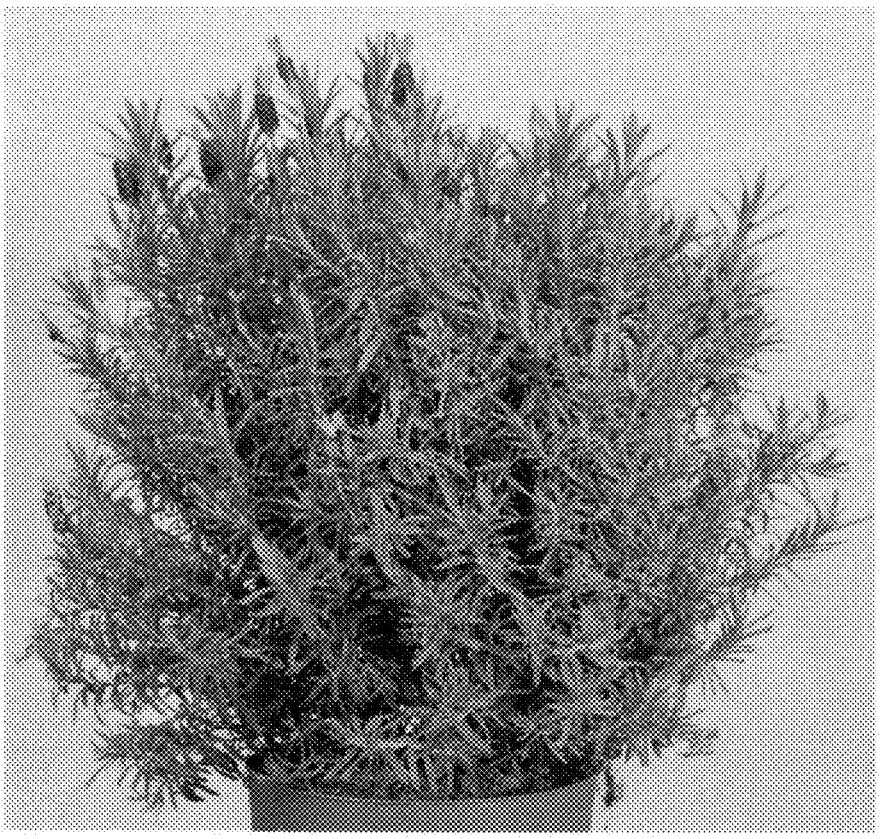

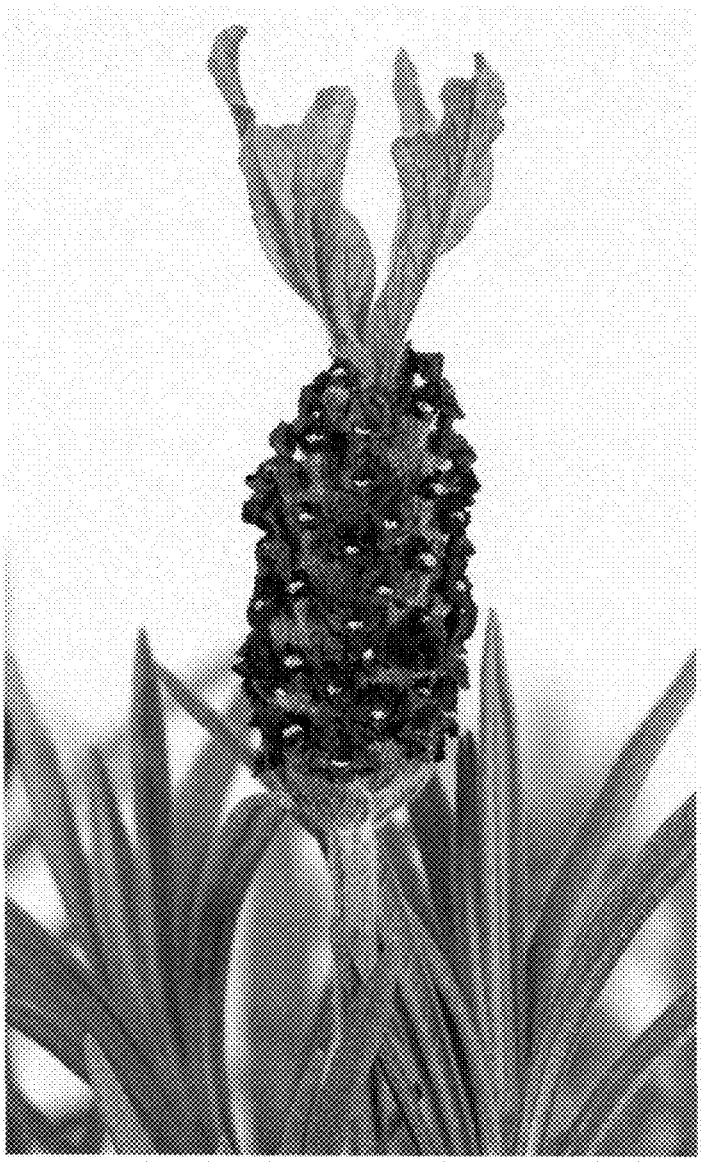

* * * * *